(12) United States Patent
Moore

(10) Patent No.: US 7,075,296 B2
(45) Date of Patent: Jul. 11, 2006

(54) INSPECTION CARRIAGE FOR TURBINE BLADES

(75) Inventor: Charles C. Moore, Hibbs, PA (US)

(73) Assignee: Siemens Power Generation, Inc., Orlando, FL (US)

( * ) Notice: Subject to any disclaimer, the term of this patent is extended or adjusted under 35 U.S.C. 154(b) by 101 days.

(21) Appl. No.: 10/984,515

(22) Filed: Nov. 9, 2004

(65) Prior Publication Data

US 2006/0097719 A1    May 11, 2006

(51) Int. Cl.
  *G01N 27/90* (2006.01)
  *G01R 33/12* (2006.01)
(52) U.S. Cl. .......................... 324/262; 324/228; 73/660
(58) Field of Classification Search ................ 324/209, 324/220, 234, 228, 236–243, 260–262; 73/660, 73/661, 779, 462
See application file for complete search history.

(56) References Cited

U.S. PATENT DOCUMENTS

| | | | |
|---|---|---|---|
| 3,739,262 A | 6/1973 | Seekins |
| 3,960,006 A | 6/1976 | Smith |
| 4,139,822 A | 2/1979 | Urich et al. |
| 4,229,796 A | 10/1980 | Garrett |
| 4,272,781 A | 6/1981 | Taguchi et al. |
| 4,282,577 A | 8/1981 | Abend et al. |
| 4,409,549 A | 10/1983 | Garner et al. |
| 4,468,620 A | 8/1984 | Vaerman |
| 4,518,917 A | 5/1985 | Oates et al. |
| 4,638,667 A | 1/1987 | Zimmer et al. |
| 4,741,203 A | 5/1988 | Willaman et al. |
| 4,803,563 A | 2/1989 | Dailey et al. |
| 4,806,848 A | 2/1989 | Demers |
| 4,811,091 A | 3/1989 | Morrison et al. |
| 4,876,505 A | 10/1989 | Osborne |
| 4,889,000 A | 12/1989 | Jaafar et al. |
| 4,962,660 A | 10/1990 | Dailey et al. |
| 4,991,441 A | 2/1991 | Nottingham et al. |
| 5,020,234 A | 6/1991 | Alkire et al. |
| 5,068,721 A | 11/1991 | Dietrich |
| 5,097,711 A | 3/1992 | Rozelle et al. |
| 5,140,264 A | 8/1992 | Metala et al. |
| 5,164,826 A | 11/1992 | Dailey |
| 5,275,052 A | 1/1994 | Luttrell et al. |
| 5,365,166 A | 11/1994 | Dailey et al. |
| 5,445,027 A | 8/1995 | Zorner |
| 5,479,826 A | 1/1996 | Twerdochlib et al. |
| 5,557,216 A | 9/1996 | Dailey et al. |
| 5,611,391 A | 3/1997 | Hyp |
| 5,611,948 A | 3/1997 | Hawkins |
| 5,689,734 A | 11/1997 | Bauer et al. |
| 5,781,007 A | 7/1998 | Partika et al. |
| 6,082,198 A | 7/2000 | Sabourin et al. |
| 6,094,989 A | 8/2000 | Twerdochlib |
| 6,420,867 B1 | 7/2002 | Goldfine et al. |
| 2003/0056595 A1 | 3/2003 | Harrold et al. |
| 2003/0095256 A1 | 5/2003 | Kitagawa et al. |

*Primary Examiner*—Jay M. Patidar

(57) ABSTRACT

An inspection carriage provides for remote inspection of the Z-shroud and snubber regions of the blades of a steam turbine, while the blades remain in the turbine. The carriage includes a non-destructive inspection probe such as a meandering wave magnetometer probe or eddy current probe mounted on a slider, so that the probe may be moved along a radial axis, skew axis, axial axis, and rotation axis. Cameras are provided on the carriage so that the probe may be remotely guided into the region to be inspected.

20 Claims, 7 Drawing Sheets

INSPECTION CARRIAGE FOR TURBINE BLADES

BACKGROUND OF THE INVENTION

1. Field of the Invention

The present invention relates to non-destructive inspection of steam turbines. More specifically, the invention provides an apparatus for performing non-destructive inspection of steam turbine blades while the blades remain within the turbine.

2. Description of the Related Art

Steam turbines typically include a plurality of rows rotating blades, with each successive row having a slightly larger diameter than the preceding row. The individual blades within each row define end regions in close proximity to the end regions of the adjacent blades, having a Z-shaped gap in between. These end regions are typically referred to as the Z-shroud region. The last, largest diameter blades in the turbine, known as the L-0 blades, also include cylindrical stand-offs at the midpoints of the blades, defining a narrow gap between the cylindrical standoffs of adjacent blades. The gap between adjacent blades at the Z-shroud and snubber regions may be about 0.15 inch. The blades make contact in these regions when a turbine is operating, due to bending and twisting of the blades, resulting in the potential for contact stresses and cracking within these regions. Additionally, the narrow gap between adjacent blades in these regions makes inspection of these regions difficult while the blades are within the turbine.

Although present turbine designs provide access to the region within the turbine behind the L-0 blade, the heat within a turbine makes it undesirable for individuals to remain in this region for extended periods of time even considering that the turbine will be off when entered. Inspection of the blades while they are in the turbine is desirable to minimize the time required for the inspection, and therefore the time during which the turbine may not be operated.

Accordingly, there is a need for a non-destructive testing apparatus for inspecting the Z-shroud and snubber regions of turbine blades without removing the blades from the turbine.

There is a further need for an apparatus permitting this inspection to be performed remotely, thereby limiting the amount of time during which an individual must be within the turbine.

SUMMARY OF THE INVENTION

The invention provides an inspection carriage for delivering an inspection probe such as a meandering wave magnetometer (MWM) probe or eddy current probe into the Z-shroud and snubber regions of a steam turbine blade.

The carriage includes a rigid hook structured to fit over the top (trailing edge) of a blade. A pair of snap-type, non-marring clamps may be secured to the leading edge (bottom) of the blade. The probe head assembly may be mounted on one end of the carriage for inspection of the Z-shroud region, or on the opposite end of the carriage for inspection of the snubber region. However, it is preferred to provide a pair of carriages, one having the probe head assembly configured for inspection of the Z-shroud, and the other having a probe head assembly configured for inspection of the snubber.

The probe head assembly includes a thin paddle to which an inspection probe such as a meandering wave magnetometer probe or eddy current probe is fastened, preferably using double-sided tape having a cushioning foam. The electronics associated with the inspection probe may be secured to the probe head assembly, below the paddle. The probe is electrically connected to the electronics using a thin, flexible connection, permitting the paddle to rotate at least 180 degrees.

Extension and retraction of the probe along a radial axis is accomplished using a radial positioning motor. The probe head assembly is secured to the carriage using a slider assembly and a lead screw. The radial positioning motor turns the lead screw to extend and retract the probe head assembly, with a position feedback encoder monitoring the position of the probe by monitoring the rotation of the lead screw.

A skew axis permits adjustment of the probe orientation from a position aligned with its radial direction of travel to an orientation that may, in some preferred embodiments, be about +/−7 degrees. A skew motor mounted on the axis probe head assembly slides a skew base plate around a curved dovetail slide. The remaining axes motors, mechanisms, and inspection probe are attached to the skew base plate. The dovetail slide is structured so that the center of the skew rotation is the center of the leading edge of the inspection probe.

An axial axis provides for movement of the inspection probe towards the surface to be inspected, biasing the probe against this surface with a force of 3.5 pounds. An axial motor moves the probe in a first direction, with springs moving the probe in the opposite direction.

The rotation axis provides the ability to rotate the inspection probe 180 degrees. This permits the probe to scan the opposing faces of adjoining blades. A limit switch limits the rotation of the inspection probe to 180 degrees to prevent damage to the connection between the probe and its associated electronics.

The paddle to which the probe is attached is inserted and retracted by remote control, thereby limiting the need to enter the hot environment of the turbine to setup and removal of the carriage. A pair of miniature video cameras is provided so that the inspector can "fly" the paddle into the Z-shroud or snubber region. A first camera, located at the top of the probe head assembly, monitors the degree to which the probe has been inserted into the inspection region. The second camera is mounted behind the paddle, looking forward from this position, so that the position of the paddle relative to the region to be inspected may be monitored. At least one camera is equipped with a light. A pair of monitors permits the inspector to monitor both cameras simultaneously.

In use, the carriage will be mounted on a blade, with the top hook hooked over the trailing edge of the blade, and the clamps secured to the bottom, leading edge of the blade. The carriage will be positioned so that the paddle is one to one and one-half inches from the Z-shroud or the snubber, whichever is to be measured. Once the carriage is mounted on the blade, the operator exits the turbine. The inspector will then insert the paddle into the region to be inspected, monitoring the position using the cameras and the encoders associated with the various motors, and will then apply an axial force to push the probe against the surface to be inspected. The inspector will perform the inspection with the probe being slowly backed out of the area to be inspected. The inspector will then repeat this procedure with the probes skewed at about +7°, and at about −7°. The inspector will then rotate the paddle 180 degrees to inspect the opposing surface, inspecting this surface by retracting the probe first aligned with the radial axis, and then at about +7° and −7° from this axis.

The present invention therefore provides an inspection carriage for delivering an inspection probe into the Z-shroud and snubber regions of the steam turbine blade. The invention further provides the ability to move the inspection probe along a radial axis, a skew axis, an axial axis, and a rotation axis. Additionally, the invention provides for securing of the inspection carriage to the turbine blade within a turbine, in a non-marring fashion, regardless of the position of the turbine blade within its plane of rotation. The invention further provides a means of performing the inspection remotely, using at least one, and preferably a pair, of cameras to permit the inspector to monitor and guide the inspection probe into the Z-shroud and snubber regions. The invention additionally provides an inspection carriage that may be used to inspect either the Z-shroud or snubber region with only minor reconfiguration of the carriage.

Accordingly, it is an object of the present invention to provide an inspection apparatus having an inspection probe capable of fitting within a narrow gap between adjacent components.

It is another object of the invention to provide a non-destructive inspection apparatus capable of inspecting different regions of a turbine blade with minor reconfiguration of the components.

It is a further object of the invention to provide a non-destructive inspection apparatus capable of being mounted on a turbine blade, and remotely performing an inspection.

It is another object of the invention to provide a carriage for non-destructive inspection of turbine blades capable of inserting either a meandering wave magnetometer probe or an eddy current probe into the region to be inspected.

It is a further object of the invention to provide an inspection carriage capable of precisely moving the inspection probe along a radial axis, skew axis, axial axis and rotational axis.

It is a further object of the invention to provide a non-destructive inspection apparatus for turbine blades capable of performing the inspection without removal of the blade from the turbine.

It is another object of the invention to provide a non-destructive inspection apparatus capable of inspecting a blade within a turbine remotely.

It is a further object of the invention to provide a non-destructive inspection carriage capable of being secured to a turbine blade in a non-marring fashion.

It is another object of the invention to provide a non-destructive inspection carriage having at least one camera and at least one light for displaying the position of the inspection probe relative to the region to be inspected to a human inspector.

It is a further object of the invention to provide a non-destructive inspection carriage that may be secured to a blade within a steam turbine regardless of the position of that blade within its rotational plane.

It is another object of the invention to provide a non-destructive inspection apparatus that will permit faster, more efficient, and higher quality inspections of high wear portions of turbine blades.

These and other objects of the invention will become apparent through the following description and drawings.

BRIEF DESCRIPTION OF THE DRAWINGS

Like reference characters denote like elements throughout the drawings.

DETAILED DESCRIPTION

Figure 1:
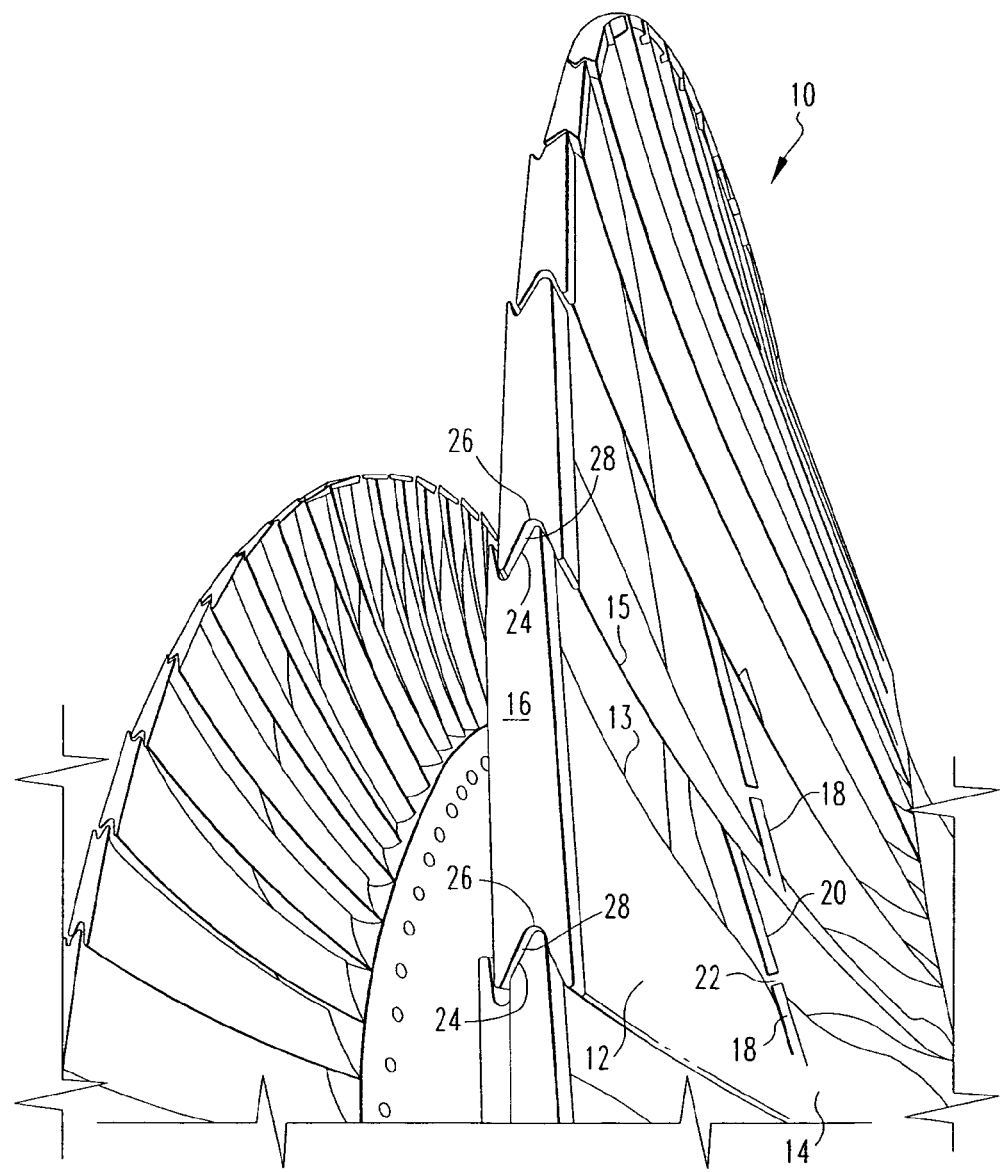
FIG. 1 is an isometric view of a turbine rotor assembly (removed from the turbine casing) for which the present invention will be used.

The present invention provides an inspection carriage for remotely inspecting the Z-shroud and snubber regions of turbine blades while the turbine blades remain within the turbine. Referring to FIG. 1, the L-0 row of turbine blades 10 includes individual blades 12, with each blade having a leading edge 13, trailing edge 15, center section 14 and an outside edge 16. The center section 14 of each blade 12 includes an upper cylindrical standoff 18 and a lower cylindrical standoff 20. The upper and lower standoff cylindrical standoff 18, 20 of adjacent blades 12 define a snubber region 22 therebetween. Likewise, the edge 16 includes an upper end 24 and a lower end 26. The upper and lower ends 24, 26 of adjacent blades 12 define a Z-shroud region therebetween. When the turbine is in use, the adjacent upper and lower standoff cylinders 18, 20, and adjacent upper and lower ends 24, 26 of adjacent edges 16, may rub against each other as the blades bend and twist. This contact can result in damaged blade coatings and/or cracked blades.

Figure 2:
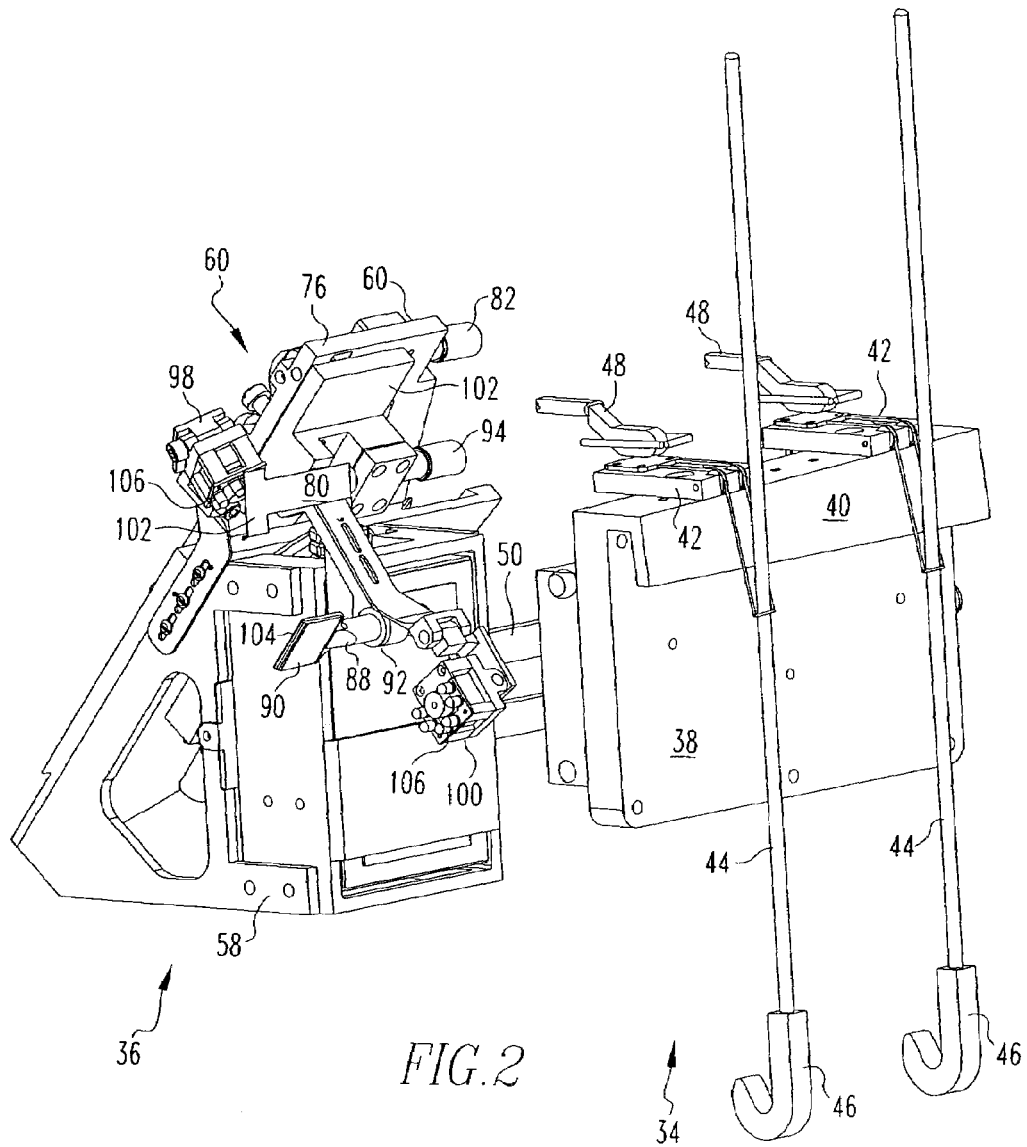
FIG. 2 is an isometric side view of an inspection carriage according to the present invention, configured for inspection of the Z-shroud region.
Figure 3:
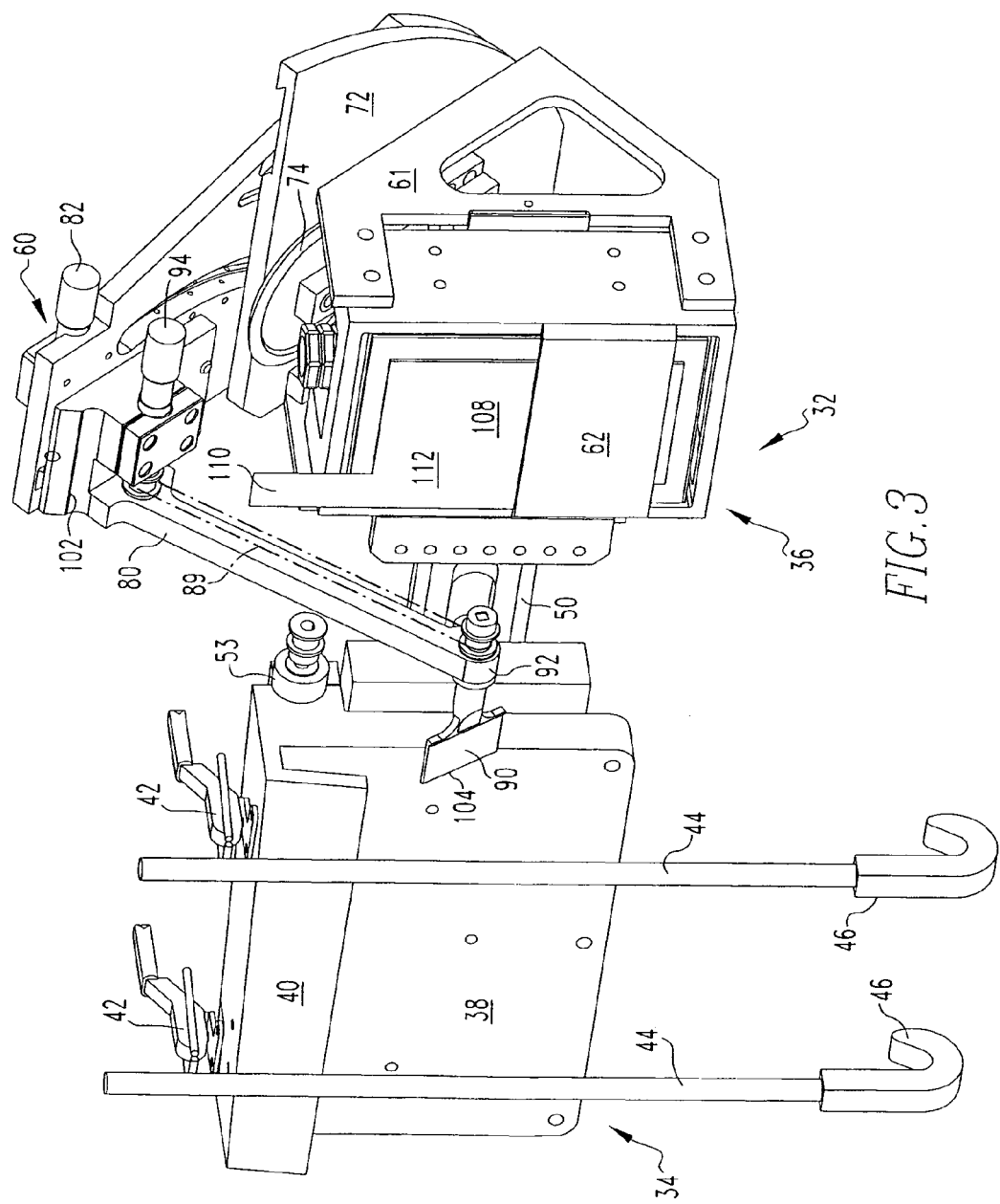
FIG. 3 is an isometric side view of an inspection carriage according to the present invention, configured for inspection of the snubber region.
Figure 4:
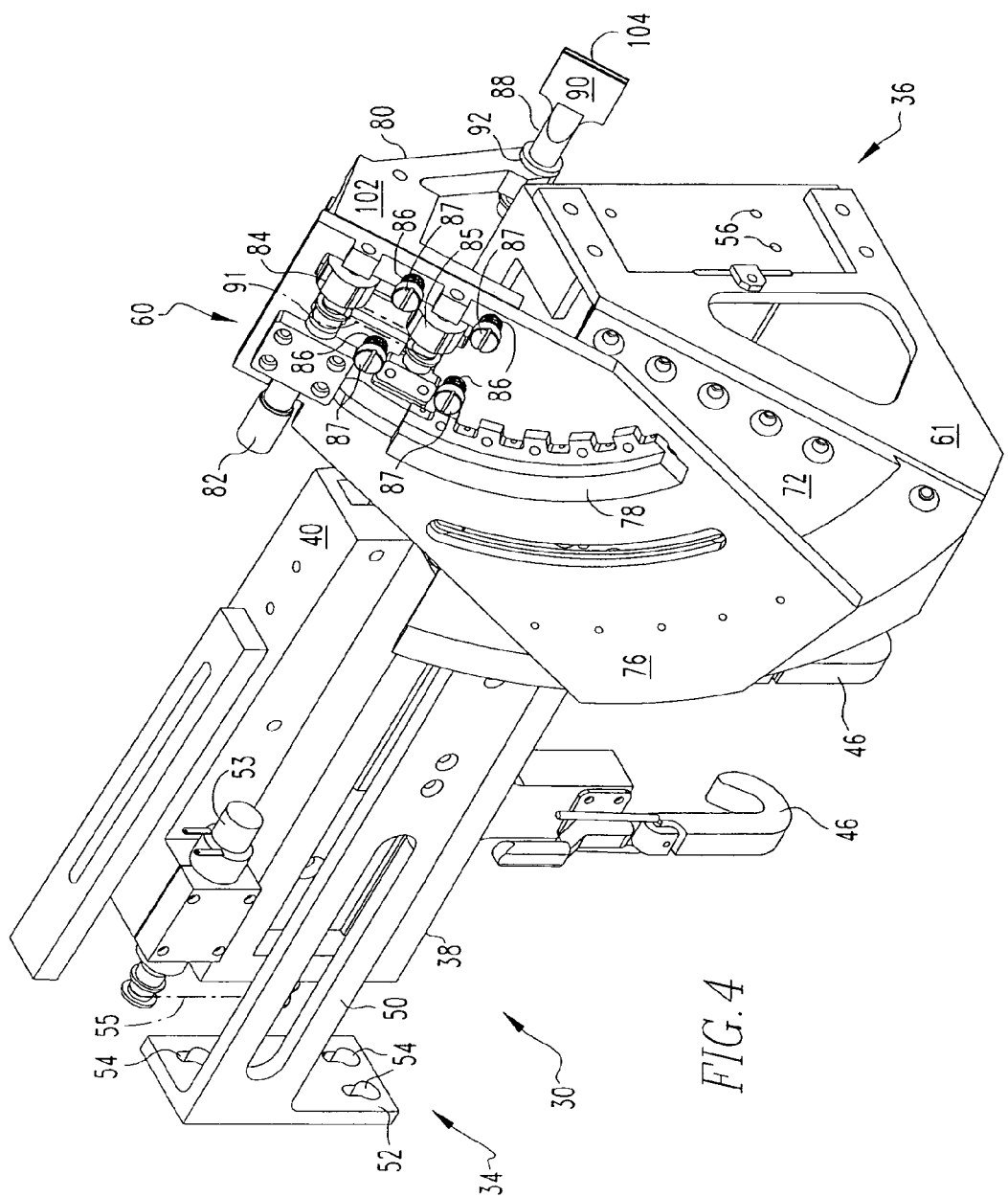
FIG. 4 is a top isometric view of an inspection carriage according to the present invention, configured for inspection of the Z-shroud region.

Referring to FIGS. 2–4, an inspection carriage of the present invention is illustrated. As FIGS. 2 and 4 illustrate a Z-shroud inspection carriage 30, and FIG. 3 illustrates a snubber inspection carriage 32. It is to be understood, however, that the same inspection carriage may, if desired, be used to inspect both the Z-shroud and snubber regions through a minor reconfiguration of the inspection carriage's components, as will be explained in further detail below. The inspection carriage 30, 32 includes a base 34 and a slider assembly 36. The base 34 includes a base plate 38 having a hook 40 along its upper edge, with the hook 40 being dimensioned and configured to fit over the trailing edge of a blade 12. The base plate 38 also includes at least one, and preferably two, non-marring snap type clamps 42 for engaging the leading edge of a blade 12. The preferred embodiments of the clamps 42 includes an elongated rod 44, which is preferably nonmetallic, terminating in a non-marring hook 46 that is structured to fit over the leading edge of a blade 12. The rods 44 are slidably mounted within the clamps 42, and may be selectively permitted to slide or resisted from sliding through the use of the clamp's actuating lever 48 as is well known to those skilled in the art of clamps. Referring to FIG. 4, the base 34 includes a beam 50 having an end flange 52. The movement of the beam 50 with respect to the base 34 of the carriage 30, 32 is controlled by a motor-driven lead screw (not shown, but well understood to those skilled in the art), powered by the motor 53 driving the drive belt 55, which turns the lead screw.

Referring back to FIGS. 2–4, the slider assembly 36 is mounted to end flange 52, for example, by bolts or screws passing through the apertures 54 within the end flange 52 and being secured within the apertures 56 defined within the slider assembly 36. Therefore, the slider assembly 36 may be secured to end flange 52 and the beam 50 installed within the base plate 38 as illustrated in FIGS. 2 and 4 to inspect the Z-shroud region, or as illustrated in FIG. 3 to inspect the snubber region.

The slider assembly 36 includes a main body 58 that is secured to one of the end flanges 52. A skew assembly 60 is pivotally secured to the main body 58.

Figure 5:
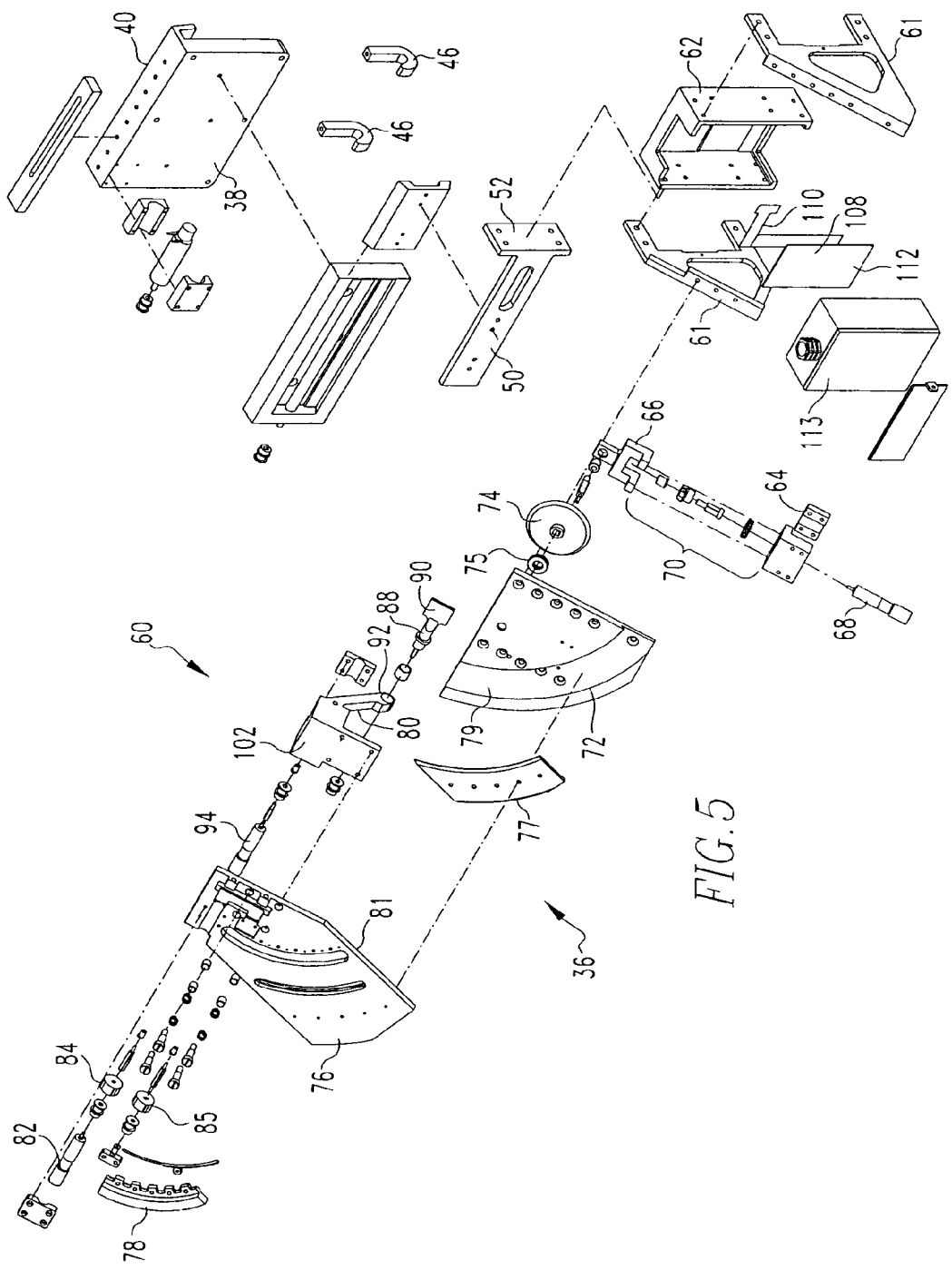
FIG. 5 is an exploded top isometric view of a slider for an inspection carriage of the present invention.

Referring to FIG. 5, the slider assembly 36 includes a pair of side plates 61 secured on either side of an enclosure holder 62. Skew motor bracket 64 and latch hook 66 secure the skew motor 68 and its associated gearing mechanism 70 to the side plates 61 opposite the enclosure holder 62. The skew dovetail 72 is secured above the latch hook 66, with a gear 74 secured therebetween and operatively engaged between the gearing mechanism 70 and gear 75. A skew plate 76 is pivotally secured above the skew dovetail 72, and includes a gear rack mount block 78 secured therein. A guide plate 77, which is dimensioned and configured to slide within the channel 79 of the skew dovetail 72 is mounted on the underside 81 of the skew plate 76. The interaction of the gear 75 and rack mount block 78 causes the skew plate 76 to pivot within its range of motion, guided by the sliding of the plate 77 within the skew dovetail 72.

An arm 80 is secured to the skew plate 76 in a manner permitting the arm 80 to be moved towards or away from the skew plates 76. In some preferred embodiments, the range of axial motion of the arm 80 towards and away from the skew plate 76 is about one inch. An axial motor 82 is mounted on the skew plate 76, and is operatively connected to the eccentric cams 84, 85 which are dimensioned and configured to bias the arm 80 away from the skew plate 76. In one preferred embodiment, the axial motor 82 is connected either directly or through a gearing mechanism to the eccentric cam 84, which is in turn connected by a drive belt 91 to the eccentric cam 85, so that both eccentric cams 84, 85 move simultaneously to push against the upper end 102 of the arm 80. At least one spring 86 biases the arm 80 towards the skew plate 76. Referring back to FIG. 4, the upper end 102 of the arm 80 may be secured to the skew plate 76 by a plurality of screws 87, with the springs 86 held between the screw heads of the screws 87 and the skew plate 76. The springs 86 will thereby bias the heads of the screws 87, and therefore the arm 80, towards the skew plate 76.

A probe 88 having a probe head 90 is rotatably mounted within the end 92 of the arm 80. Rotation of the probe 88 is controlled by a rotational motor 94, mounted on the skew plate 76, and operatively connected to the probe 88 by a drive belt 89.

Referring back to FIGS. 2–4, a pair of cameras 98, 100 are mounted on the slider assembly 36. The camera 98 is mounted at the upper end 102 of the arm 80, oriented to view the leading edge 104 of the probe head 90 in a direction substantially perpendicular to the direction of extension and retraction of the slider assembly 36. The camera 100 is mounted at the end 92 of the arm 80, and is oriented to view the probe head 90 from behind, in a direction substantially parallel to the direction of extension and retraction of the slider assembly 36. Either or both of the cameras 98, 100 may include a light source, for example, the light bars 106.

Referring to FIG. 3, an MWM sensor apparatus 108 is illustrated within the enclosure holder 62. It is to be understood that the MWM sensor apparatus, could, if desired, be replaced with an eddy current apparatus.

The MWM sensor apparatus 108 includes a sensor portion 110 extending upwards from an electronics portion 112, with the electronics portion 112 being secured within the enclosure holder 62, held in place between the enclosure holder 62 and MWM electronics box 113 (FIG. 5). The sensor portion 110 may be secured to the probe head 90, with one preferred means being double-sided tape with foam. Limit switches (not shown, but well known to those skilled in the art) limit the rotation of the rotational motor 94 so that the range of rotation of the probe head 90 does not exceed about 180°, thereby preventing over-rotation of the probe head 90 from damaging the sensor portion 110.

Figure 6:
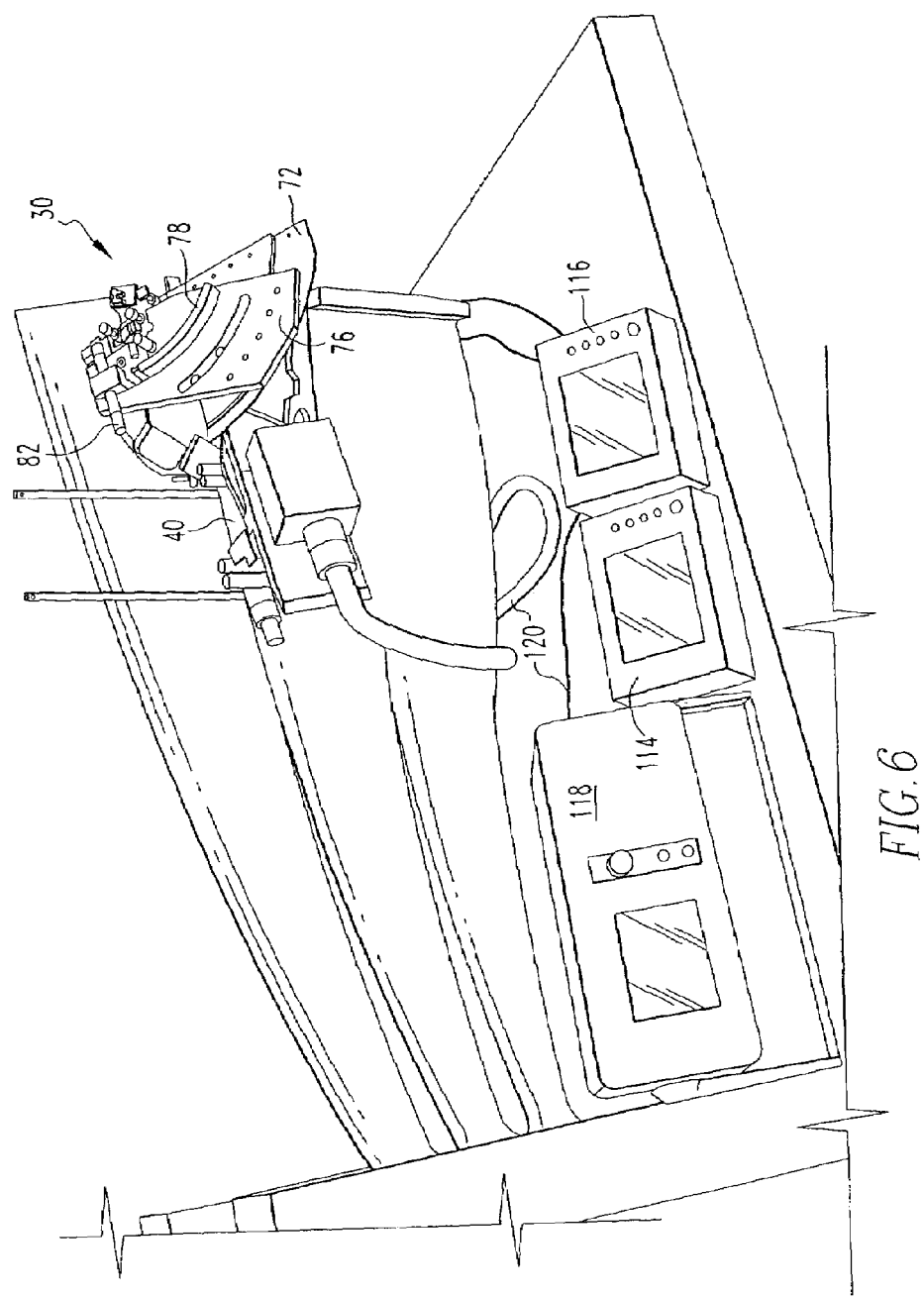
FIG. 6 is an isometric view of a mock setup of an inspection carriage according to the present invention and its associated monitors and data collection electronics.

Referring to FIG. 6, an inspection carriage 30 is illustrated along with the equipment needed to remotely operate the inspection carriage 30. A pair of monitors 114, 116 permit the inspector to view the images from both cameras 98, 100 simultaneously while moving the probe head 90. Motor control box 118 is used to control the radial motor 53, skew motor 68, axial motor 82, and rotational motor 94. The monitors 114, 116 and motor control box 118 are connected to the inspection carriage 30 by cables 120 sufficiently long to permit the inspection to be performed from outside of a steam turbine while the carriage is installed on a blade within the steam turbine.

Figure 7:
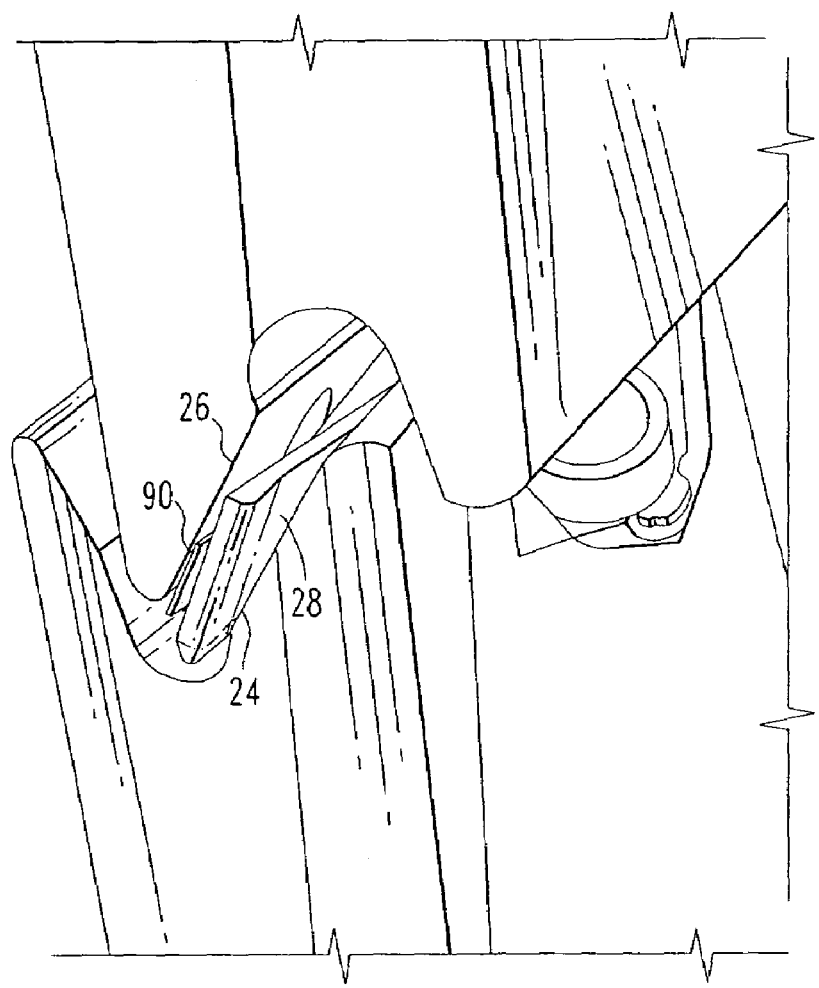
FIG. 7 is an isometric end view of an inspection probe of the present invention within the Z-shroud region.

In use, an inspection carriage 30, 32 will be installed on a blade 12 within a turbine, usually with the blade 12 at the three o'clock position, and with the turbine being manually rotated so that each blade is in this position when the inspection carriage is installed. However, the carriage may be installed upon any blade at any position within the turbine. Typically, an individual will enter a manhole in the turbine behind the blades to be inspected while the turbine is not operating, hook the top hook 40 over the trailing edge 15 of the blade 12, and secure the clamps 42 over the leading edge 13 of the blade 12. The individual will then exit the turbine. The individual performing the inspection will, using the cameras 98, 100, extend the probe head 90 into either the Z-shroud region 28 or snubber region 22 using the radial motor 53, while also using the rotational motor 94 to align the probe head 90 with the angle of the Z-shroud region 28 or snubber region 22. Initially, the skew angle will be left at zero. Referring to FIG. 7, a probe head 90 within the Z-shroud region 28 is illustrated. The axial motor 82 or springs 86 will move the probe head 90 so that the sensor portion 110 is pressed against either the end surface of the upper standoff cylinder 18 or lower standoff cylinder 20, or the upper ends 24 or lower ends 26 of the outside edge 16. The radial motor 53 will be actuated in the opposite direction, thereby retracting the probe 90 from the inspected region, as data is collected and sent to a computer with the appropriate software (not shown and well-known in the art of MWM inspection) for analysis and conversion to graphical form. An example of a preferred software package is presently available from Jentek Sensors, Inc., located at 200 Dexter Avenue, Watertown, Mass. 02472-4238. Next, the skew motor 68 is actuated to rotate the skew plate 76, thereby pivoting the probe head 90 around the center point of its leading edge 104. A suggested skew angle is about +7°. The radial motor 53 will again be actuated to insert the probe head 90 into either the Z-shroud region 28 or snubber region 22. Again, the axial motor 82 or springs 86 is used to bias the sensor portion 110 against the surface to be inspected, and the radial motor 53 is actuated to withdraw the probe head 90 from either the Z-shroud region 28 or snubber region 22. Next, the skew motor 68 is actuated to rotate the skew plate 76 and therefore probe head 90 to another skew angle, for example, about −7°. The radial motor 53 is again actuated to insert the probe head 90 into either the Z-shroud region 28 or snubber region 22. The axial motor 82 or springs 86 is again used to bias the sensor portion 110 against the surface to be inspected, and the radial motor 53 is actuated to withdraw the probe head 90 as the data is collected. One of the two surfaces within the Z-shroud region 28 or snubber region 22 has therefore been inspected with the MWM sensor portion 110 at a skew angle of 0+7°, and −7°.

The rotational motor 94 is actuated to rotate the probe head 90 about 180° to inspect the opposing surface within the Z-shroud region 28 or snubber region 22. The radial motor 53 is actuated to insert the probe head 90 into the Z-shroud 28 or snubber region 22, with the skew angle set to about 0°. The axial motor 82 or springs 86 is used to bias the probe head 90 against the surface to be inspected so that the sensor portion 110 contacts this surface. The radial motor 53 is used to retract the probe head 90 as the sensor 108 collects the MWM data. The skew motor 68 is actuated to rotate the skew plate 76 and probe head 90 so that the probe head 90 is skewed to a first angle, for example, about +7°. The radial motor 53 is actuated to insert the probe head 90 into the Z-shroud region 28 or snubber region 22. The axial motor 82 or springs 86 biases the sensor portion 110 against the surface to be inspected, and the radial motor 53 is again actuated to withdraw the probe head 90 as the inspection is performed. Lastly, the skew motor 68 is actuated to rotate the skew plate 76 and probe head 90 to a second skew angle, for example, about −7°. The radial motor 53 is actuated to insert the probe head 90 into the Z-shroud region 28 or snubber region 22. The axial motor 22 or springs 86 biases the sensor portion 110 against the surface to be inspected as the radial motor 53 retracts the probe head 90 from the Z-shroud region 28 or snubber region 22. At this point, one complete inspection of one Z-shroud region 28 or snubber region 22 has been completed, and the carriage may be moved to the next turbine blade 12.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. An inspection carriage, comprising:
    a main body having means for securing to a blade of a turbine;
    a slider assembly reciprocably mounted on the main body, the slider assembly being structured for movement between a retracted position and an extended position;
    a probe head rotatably mounted on the slider assembly, the probe head having a rotation axis structured for rotation about an axis substantially parallel to the direction of movement of the slider, and an axial axis structured for lateral movement of the probe head in a direction substantially perpendicular to the slider, the probe head being structured to fit within a Z-shroud or a snubber region of a turbine, and to perform a non-destructive inspection of the Z-shroud or snubber region of the turbine.

2. The inspection carriage according to claim 1, wherein the means for securing the carriage to the blade to the turbine include a hook structured to receive one edge of the blade, and a clamp structured to receive an opposing edge of the blade.

3. The inspection carriage according to claim 1, further comprising a motor-driven lead screw for extending and retracting the slider assembly.

4. The inspection carriage according to claim 1:
    further comprising a skew axis rotatably mounted on the slider assembly; and
    wherein the probe head is mounted on the skew assembly.

5. The inspection carriage according to claim 4, wherein:
    the probe head includes a leading edge having a center; and
    the skew axis is dimensioned and configured to rotate the probe head substantially about the center of the leading edge and substantially within a plane defined by the probe head.

6. The inspection carriage according to claim 4, wherein the skew axis includes a motor-driven skew plate.

7. The inspection carriage according to claim 6, wherein the skew plate is dimensioned and configured to rotate the probe head through an arc of about 14°.

8. The inspection carriage according to claim 1, wherein the probe head is selected from the group consisting of an eddy current probe head and a meandering wave magnetometer probe head.

9. The inspection carriage according to claim 1, wherein the axial axis includes a motor-driven eccentric cam for moving the probe head in a first direction.

10. The inspection carriage according to claim 1, wherein the axial axis includes a spring for moving the probe in a second direction.

11. The inspection carriage according to claim 1, wherein the axial axis is structured to move the probe head laterally through a range of motion of about one inch.

12. The inspection carriage according to claim 1, wherein the carriage is structured to provide about 3.5 lb. of force upon the probe head in the lateral direction.

13. The inspection carriage according to claim 1, wherein the rotation axis includes a rotation motor.

14. The inspection carriage according to claim 13, wherein the rotation axis includes a drive belt connected between the rotation motor and an axis of rotation of the probe head.

15. The inspection carriage according to claim 1, wherein the rotation of the probe head is controlled by limit switches.

16. The inspection carriage according to claim 15, wherein the probe head is structured for 180° of rotation.

17. The inspection carriage according to claim 1, wherein the radial axis, the skew axis, the axial axis, and the rotation axis include means for receiving control signals from outside the turbine.

18. The inspection carriage according to claim 1, further comprising at least one camera and a monitor associated with the at least one camera, the at least one camera being structured to display the insertion of the probe head into the Z-shroud or snubber region on the monitor.

19. The inspection carriage according to claim 18, further comprising:
    a first camera mounted on the slider assembly adjacent to the leading edge of the probe head and structured to display the leading edge,
    a second camera mounted on the slider assembly behind the probe head and structured to display the angular relationship between the probe head and the Z-shroud or snubber region.

20. The inspection carriage according to claim 18, further comprising a light structured to light a region monitored by the at least one camera.

* * * * *